United States Patent [19]

Magistro

[11] Patent Number: 4,874,858
[45] Date of Patent: Oct. 17, 1989

[54] TRIAZINE-CONTAINING MULTISILANE COUPLING AGENTS FOR COATING GLASS FIBERS, FOR ADHESIVES, AND FOR PROTECTIVE COATINGS

[75] Inventor: Angelo J. Magistro, Brecksville, Ohio

[73] Assignee: The B. F. Goodrich Company, Akron, Ohio

[21] Appl. No.: 173,898

[22] Filed: Mar. 28, 1988

[51] Int. Cl.$^4$ .............................................. C07D 251/54
[52] U.S. Cl. ..................................... 544/196; 544/197
[58] Field of Search ................................. 544/196, 197

[56] References Cited

U.S. PATENT DOCUMENTS 3,709,884  1/1973  Dexter et al. ........................ 544/196

FOREIGN PATENT DOCUMENTS 0174262  12/1986  European Pat. Off. ............ 544/196

OTHER PUBLICATIONS

"Organofunctional Silanes—Multi-Functional Components for Glass Fibers", by Marsden, J. E. and Pepe, E. J., 40th Annual Conference, Reinforced Plastics/Composites Institute, The Society of the Plastics Industry, Inc., Jan. 28–Feb. 1, 1985.

"New Potential Silane Coupling Agents", by David F. Sounik and Malcolm E. Kenney, *Polymer Composites*, vol. 6, No. 3, Jul. 1985.

*Primary Examiner*—Mary C. Lee
*Assistant Examiner*—Robert C. Whittenbaugh
*Attorney, Agent, or Firm*—James R. Lindsay; Nestor W. Shust; Alfred D. Lobo

[57] ABSTRACT

At least three, and as many as eighteen, most preferably at least nine, crosslinking sites are provided through the alkoxy groups in multiple chains on a triazine ring (hence "multisilane"), on a single molecule of the multisilane. The multisilane, useful as a coupling agent, is formed by reacting a triazine-containing compound with a suitable aminoalkyl-alkoxysilane, or, alkyl-aminoalkyl-alkoxysilane in either an anhydrous, or an aqueous liquid medium. A size containing the multisilane, enhances the reinforced properties of organic synthetic resinous materials in which the fibers are used, and most particularly those of rigid poly(vinyl chloride) (PVC) with which it provides cohesive bonding of glass fiber surfaces. Glass fibers coated with a basic film former and the multisilane are covalently bonded on the one hand through some of at least nine alkoxy groups on each of the multisilane molecules, to Si atoms of a glass surface, and on the other hand, through at least some of the amine groups on each of the molecules, to the vinyl chloride (VC) resin in a reaction which involves allylic chloride bonds in the VC resin. The multisilane is effective in adhesives for a wide variety of materials, and in protective coatings.

2 Claims, No Drawings

TRIAZINE-CONTAINING MULTISILANE COUPLING AGENTS FOR COATING GLASS FIBERS, FOR ADHESIVES, AND FOR PROTECTIVE COATINGS

BACKGROUND OF THE INVENTION

This invention relates to novel multipurpose triazine-containing multisilane compounds useful as coupling agents, adhesives, protective coatings and the like; to fillers and glass fibers coated with the coupling agents; to a process for preparing the compounds; and to glass fiber reinforced (GFR) composites in which such coated glass fibers in the form of yarns, cords, strands, and fabrics, collectively referred to herein as "glass fibers" or simply "fibers" for brevity, are used.

The multisilane compounds are obtained by a reaction of cyanuric chloride with an aminoalkyl-alkoxysilane or alkyl-aminoalkyl-alkoxysilane, together referred to as "alkoxysilanes" for brevity.

It is suggested that bis-trimethoxysilyl coupling agents provide increased crosslinking of the coupling agent in the interface region by creating six (6) crosslinking sites—double that of a conventional trialkoxysilane coated filler—hence result in improved adhesion. See "Surface Modifiers: They are Becoming More Versatile" by P. A. Toensmeier *Modern Plastics* pg 55 May 1987. This is attributed to multiple bonding of atoms, which creates a surface adhesion expected to be not only strong but moisture- and corrosion- resistant. Though the bonds are hydrolyzable, equilibrium is such that they reform easily, and the additives can be used in any resin using silanes.

This invention specifically provides a multisilane which provides at least nine (9) crosslinking sites, and has several other advantages which make it an exceptional coupling agent.

More specifically, this invention relates to multisilane coupling agents employed in a sizing composition for glass fibers and other siliceous fillers having analogous reaction characteristics. It will be recognized that fibers are a particular form of filler used in those instances where reinforcement is sought to enhance the inertness, strength and other physical charateristics of a reinforced solid synthetic resinous material. For example, an essential characteristic of the such fillers is that chemical groups on their surface are hydrophilic so that only a weak bond can be established between the synthetic resin and the surfaces of the fibers. Such bonding as is established is vitiated by immersion in water, or even by exposure to high humidity. To enhance the bonding relationship a plethora of anchoring or coupling agents and sizing systems have been used, none of which are more relevant than the disclosure of the bis-trimethoxysilyl coupling agents which focussed the desirablity of providing several crosslinking sites.

It must be borne in mind that a coupling agent alone provides neither adequate lubricity or bonding for processing fibers, nor adequate protection against destruction of the fibers' surfaces by mutual abrasion. Hence it is necessary to employ the coupling agent in a dilute aqueous "size" which is applied to the fibers in a well known manner so as to provide a thin coating, typically less than 1 micron thick. It is in such sizing compositions that the coupling agents of this invention, prepared in an aqueous medium, are used.

To promote adhesion between other than a glass fiber surface and a solid organic polymer, for example a polycarbonate, the coupling agents may be prepared in an essentially anhydrous medium and applied to the surface which may then be secured to the polycarbonate. However, some resins, such as rigid poly(vinyl chloride) (PVC) are notably far more difficult to bond to other surfaces, particularly large glass or metal surfaces PVC is also particularly difficult to reinforce with glass fibers than other resins, for well known reasons set forth in U.S. Pat. No. 4,536,360 to D. Rahrig, and the multisilanes are unique in that they provide performance comparable to that obtained with the conventional alkoxysilanes used in the '360 patent. Such comparable performance is obtained because these multisilanes are able to interact with PVC through the same chemistry as that delineated in the Rahrig '360 patent, namely generation of an allylic chlorine (Cl) moiety in the vinyl chloride chain.

SUMMARY OF THE INVENTION

It has been discovered that at least three, and as many as eighteen crosslinking sites through the alkoxy groups in multiple chains on a triazine ring (hence "multisilane"), may be provided on a single molecule of an alkoxysilane, useful as a coupling agent, by reacting a triazine-containing compound with a suitable aminoalkyl-alkoxoysilane, or, alkyl-aminoalkyl-alkoxysilane in either an anhydrous, or an aqueous liquid medium.

It has also been discovered that providing glass fibers with a thin coating of "size" (size-coating) in which the essential coupling agent is the aforementioned triazine-containing multisilane, enhances the reinforced properties of organic synthetic resinous materials in which the fibers are used, and most particularly of rigid poly(vinyl chloride) (PVC).

It is therefore a general object of this invention to provide a multisilane useful as a coupling agent which can be incorporated in a size, thereby producing a size which has desired processing characteristics for the production of fibers into yarns and fabrics, and the desired performance characteristics which will allow better bonding of the sized fibers to synthetic resinous materials, and particularly to PVC.

It is a specific object of this invention to provide a triazine-containing multisilane which contains at least nine functional groups which are capable of strong and preferential attachment to glass fiber surfaces, as well as being adapted to provide attachment by covalent bonding to after-applied organic polymers.

It is another specific object of this invention to provide a glass fiber coated with (i) a multisilane capable of being covalently bonded on the one hand through some of at least nine alkoxy groups on each of its molecules, to Si atoms of a glass surface, and on the other hand, through at least some of the amine groups on each of its molecules, to the VC resin in a reaction which involves C=C bonds in the VC resin, and (ii) a polymer film former.

DETAILED DESCRIPTION OF PREFERRED EMBODIMENTS

The triazine-containing multisilane of the present invention is obtained from the reaction product of an alkoxy silane having either alkylenic or arylenic moieties therewithin, with a triazine compound such as cyanuric chloride or an alkoxyalkylmelamine having at least three functional groups.

The alkoxysilane is represented by the structure:

$$\overset{H}{\underset{|}{Z-N}}-X-\overset{R'_n}{\underset{|}{Si}}-(OR)_{3-n}$$

wherein X represents a divalent radical selected the group consisting of $C_1-C_{10}$ alkylene $$-(CH_2)_{1-10},$$

and $C_6-C_{20}$ aralkyl;

R represents $C_1-C_5$ lower alkyl;

R' represents H, $C_1-C_8$ alkyl, phenyl, or $C_7-C_{18}$ aralkyl;

n has a value of 0 or 1; and,

Z is selected from the group consisting of H, monovalent lower alkyl, and an amino radical.

When Z is an amino radical the alkoxysilane is represented by the structure:

$$H-\overset{H}{\underset{|}{N}}-X_1-\overset{H}{\underset{|}{N}}-X_2-\overset{R'_n}{\underset{|}{Si}}-(OR)_{3-n}$$

wherein $X_1$ and $X_2$ are the same or different divalent $C_1-C_{10}$ alkylene groups.

Preferred multisilanes are formed by the reaction of an aminoalkyl-alkoxysilane, or an alkyl-aminoalkyl-alkoxysilane, preferably in the presence of a suitable acid catalyst such as p-toluene sulfonic acid, with a triazinering containing compound in which the 2, 4, and 6 positions are functional groups providing three or six sites easily substitutable with the alkoxysilane, most preferably cyanuric chloride, or, a hexaalkoxyalkyl-melamine such as hexamethoxymethylmelamine (HEMA) having the structures

[triazine ring with Cl, Cl, Cl substituents] and

[triazine ring with $N(CH_2OCH_3)_2$, $N(CH_2OCH_3)_2$, $N(CH_2OCH_3)_2$ substituents]

respectively. After reaction, the residue of the alkoxysilane on the substitutable sites results in a multisilane having a structure selected from

[triazine ring with (Q)N-H, N(Q)-H, N(Q)-H substituents] and

[triazine ring with $(QHNH_2C)_2N$, $N(CH_2NHQ)_2$, $N(CH_2NHQ)_2$ substituents]

wherein Q, the residue of the alkoxysilane, represents $$-X-\overset{R'_n}{\underset{|}{Si}}-(OR)_{3-n} \text{ or, } -X_1-N-X_2-\overset{R'_n}{\underset{|}{Si}}-(OR)_{3-n}$$

Preferred alkoxysilanes are: 3-aminopropyl-triethoxysilane, $H_2N-(CH_2)_3-Si-(OC_2H_5)_3$ commercially available as A-1100 from Union Carbide; aminomethyl-triethoxysilane, $H_2N-(CH_2)-Si-(OC_2H_5)_3$; 2-aminoethyl-aminopropyl-trimethoxysilane, $H_2N-(CH_2)_2-NH-(CH_2)_3-Si-(OCH_3)_3$ commercially available as A-700 and Z-6020 from Union Carbide and Dow, respectively; and, 2-aminoethyl-aminopropyl-methyl-dimethoxysilane, $$H_2N-(CH_2)_2-NH-(CH_2)_3-\overset{CH_3}{\underset{|}{Si}}-(OCH_3)_2.$$

The molar ratio of the triazine ring-containing compound and the alkoxy silane is selected so that the desired alkoxy functionality, on average, is obtained in the multisilane formed. Thus, it will be evident that, for example with cyanuric chloride, reaction with an equimolar amount of $H_2N-(CH_2)_2-NH-(CH_2)_3-Si-(OCH_3)_3$ will result, for the most part, in a monosilane (single aloxysilane substituent) having three methoxy groups, and two Cl atoms remaining on the triazine ring which would typically be hydrolyzed if the resulting monosilane is to be used as a coupling agent. It will be equally evident that even a disilane having six methoxy groups, produced by the reaction of cyanuric chloride with two equivalents of A-700 will not be as effective a coupling agent as a trisilane with nine methoxy groups, the latter produced by reaction with three equivalents of A-700, particularly as the trisilane requires no additional hydrolysis step.

Hence in the most preferred embodiment, for use of the multisilanes as coupling agents, a stoichiometric amount of alkoxysilane is used which will replace all substitutable groups on the triazine ring-containing reactant, and, in some cases, a slight excess over the stoichiometric to ensure complete substitution.

The excellent reactivity of the reactants in the presence of a catalytic amount of an organic base or Bronsted acid permits the reaction to take place by directly reacting the triazine ring-containing compound with liquid alkoxysilane in the absence of solvents. The amount of catalyst used is not narrowly critical ranging from about 0.1 to about 1%, preferably from 0.2 to about 0.5% by weight of the alkoxysilane used. If desired, as it may be when the multisilane is to be used as in an adhesive, a solvent may be used which is unreactive with the reactants under the conditions of reaction. Depending upon the specific application in which the multisilane is to be used as an adhesive, the solvent is typically chosen from aliphatic and cycloaliphatic hydrocarbons, alkyl, aryl and alkaryl ethers, aliphatic alcohols, chlorinated and fluorinated hydrocarbons, and the like.

Quite surprisingly, the reaction does not result in a significant amount of polymerization which would be expected because of the self-catalyzing effect of the alkoxysilane reactant with the multisilane formed. More surprising is that in most instances, the reaction may also be carried out in water, in which the product multisilane is soluble because of the multiple alkoxy groups, without internally crosslinking them. By "internal crosslinking" I refer to the effect of the presence of water on the substituent multisilane chains in the product, which effect would be expected to result in the crosslinking of alkoxy groups of one multisilane molecule with those of another multisilane molecule, and to a much lesser extent, of the same multisilane molecule. It will be remembered that the self-catalyzing effect of the basic multisilane and the multisilane formed is based on this reaction, as is the polymerization of an alkoxysilane in water. This latter reaction is the basis for the "aging" of an alkoxysilane size before it is applied to glass fibers.

The alkoxy groups also provide sites for external crosslinking. By "external crosslinking" I refer to the reaction of alkoxy groups with OH groups attached to Si atoms in a silica glass, which results in a Si—O—Si (siloxy) bond in which the O atom is covalently bonded to the Si atoms. It is to this external crosslinking that the bonding produced by the coupling agent, is attributed.

The multisilane produced by reaction of an alkoxysilane with a triazine ring-containing compound proceeds even at room temperature and ambient pressure, though it is more preferably carried out at elevated temperature and pressure for commercially acceptable efficiency, in an inert atmosphere. Typically the reaction is carried out in water, or a solvent, in an argon atmosphere, at a temperature below which there is substantial internal crosslinking. When the reaction is carried out in water or tetrahydrofuran (THF) as solvent, the reaction may be carried out at reflux temperature at a pressure in the range from 1 to about 10 atm (atmospheres) or higher, though no substantial advantage is to be realized from greater pressures. When the desired stoichiometric amounts of reactants are used, the reaction is allowed to proceed until an infrared (IR) absorption and nuclear magnetic resonance (NMR) spectroscopic analyses show that all the alkoxysilane reactant is consumed. The reaction is then stopped simply by cooling the reaction mass, optionally with the addition of a small amount of dilute organic or inorganic acid, as is known in the art.

Where the multisilane is to be used for coating glass fibers for reinforcing PVC, the multisilane is desirably slightly basic, and is allowed to age so as to allow partial hydrolysis of the alkoxy groups bound to the Si atoms of the multisilane to form a prepolymer, and provide a sufficient amount of remaining alkoxy groups for the desired bonding of the multisilane to the glass fibers. The amino groups ensure later reactivity with the PVC enhancing the strength of the interfacial bond between the glass and PVC surfaces.

The multisilane formed may be applied directly by spraying or brushing a thin coating onto a surface, or by incorporating the multisilane into an adhesive which is applied to a surface, or by incorporating the multisilane into a synthetic resinous material which is to be bonded to a surface.

If applied to a surface to which a resin is to be bonded, the coating of multisilane is preferably from about 0.1 to about 10 microns thick, preferably from about 1 to about 5 microns. If the multisilane is incorporated into the resin, the amount used is typically enough to provide the maximum bonding to the surface, as evidenced by the physical properties of the bonded surface in a composite.

The triazine ring provides extreme stability and desirable basicity in addition to that provided by the primary and secondary amine groups in the alkoxysilane chains. Because the surface at which bonding is desired is functionalized with both alkoxy groups, and primary and secondary amine groups, the latter particularly provide reactive sites for covalent adhesive bonding of numerous synthetic resinous materials reactive with them (the amine groups). Among commonly used polymeric materials are polycarbonates such as poly(diphenyl-2,2'-propanecarbonate) and poly(diethyleneglycol-bisallyl-carbonate); polyacrylates, polymethacrylates such as polymethylmethacrylate, polyesters such as poly(ethyleneterephthalate); epoxy resins; polyisocyanates; polyacrylonitrile; polyetherether ketone (PEEK); polyarylene polyethers; polyimides; polyacetals; polysulfones; polyethersulfones; polystyrenes; copolymers of styrene with acrylonitrile and acyrlonitrile-butadiene; PVC and the like.

The multisilanes are best adapted for use in those instances where first and second material are to be bonded through alkoxy groups which are covalently bonded to the first material, and amine groups which are covalently bonded to the second material.

The multisilane is especially well adapted for reinforcing PVC with glass fibers to produce thermoplastic, glass fiber reinforced ("GFR") PVC, and chlorinated poly(vinyl chloride) ("CPVC") which homopolymers are commonly available as rigid PVC and CPVC, and are either individually or together referred to herein as "VC homopolymer"; and to copolymers of vinyl chloride ("VC") with a copolymerizable monomer, in which copolymers VC is present in an amount sufficient to generate an allylic chlorine (Cl) moiety in the VC chain, represented thus:

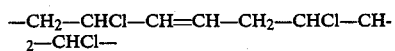

under thermoforming conditions. The copolymers may be postchlorinated provided there are sufficient runs of 10 or more C atoms in VC chains to generate reactive allylic Cl moieties. Such copolymers of VC, optionally postchlorinated, and VC homopolymer are generically referred to herein as "VC resin".

The multisilane is used as coupling (or keying) agent (sometimes referred to as 'finish') which is essential, in combination with certain polymeric film formers used in the production of glass fibers, most preferably E glass, to provide the strength in my GFR VC resin composites.

The multisilane is coated in aqueous sizing solution, suspension, or emulsion consisting essentially of water in which it is dispersed with a film former, lubricant, surface active agent, "antistat", plasticizer and the like, sometimes with a water-soluble colloid to provide the necessary stability for the dispersed polymeric film former. It is important to use a satisfactory combination of multisilane and film former in the "size" for a particular application, though the choice of film former for effective use with the multisilane is not narrowly critical.

It is known that the essential qualification of a size found satisfactorily to fulfil the strengthening function of glass fiber in VC resin is its (the size's) ability to generate allylic chlorine (Cl) moieties in a zone adjacent the surface of each glass fiber ("fiber-resin interface") where the moieties can react with the primary amine moiety of the coupling agent. This concept is taught and illustrated in U.S. Pat. No. 4,536,360 to Rahrig, the disclosure of which is incorporated by reference thereto as if fully set forth herein. The specific effective combination disclosed therein for a VC resin is (a) an aminosilane coupling agent, and, (b) a polymer film former of a ring-opened lower alkylene oxide containing 1 to 4 carbon atoms as an essential component in a repeating unit, for example poly(ethylene oxide:propylene glycol) ("PEO"), optionally containing another copolymerizable component. With the use of the multisilane, the choice of film former is not so limited.

The PVC homopolymer is commercially available rigid PVC obtained by either the mass or suspension polymerization techniques, in the form of porous solid macrogranules. Macrogranules of PVC which are converted to CPVC will typically have an average diameter in excess of 20 microns, with a preponderance of particles in excess of 50 microns in diameter. Suspension polymerized PVC deisrably has a porosity in the range from about 0.22 to about 0.35 cc/g, a surface area in the range from about 0.6 $m^2/g$ to about 3 $m^2/g$, and an inherent viscosity in the range from about 0.53 to about 1.2, that is, having a relatively high molecular weight. The mol wt may be related to its inherent viscosity which is determined as taught in U.S. Pat. No. 4,412,898. The most commonly used PVC resins have an inherent viscosity in the range from about 0.53 to about 1.1, or slightly higher, and are referred to as "rigid PVC". Such a resin is commercially available from The B. F. Goodrich Company under the Geon ® 110X346 designation.

The reaction of the multisilane with VC resin occurs through allylic Cl sites in the resin. It is this reaction which provides a covalent chemical linkage between the VC resin and the multisilane-treated glass fibers. Evidence for this conclusion is based on a comparison of the thermal stability of PVC on a two-roll mill, in the presence of multisilane, with the stability in the absence of the multisilane. The proton magnetic resonance spectra and the resonance Raman spectra of products I obtained by mixing treated glass fibers and PVC on the two-roll mill, confirm the fact that a reaction occurs between the multisilane and PVC during mixing, and that this reaction involves the C=C bonds present in the PVC. Whether these bonds are generated in a sufficient quantity at or near the interface of glass surface and VC resin, to strengthen the reinforcing effect of the glass fibers appreciably, depends on the basicity of the film former and the characteristics of the repeating units in its generic structure.

The effectiveness of the multisilane with VC resin derives from its function as a reactant to couple the allylic chloride bonds generated at the interface of the resin. Confirmation is provided with evidence that glass, coated with multisilane and blended with PVC, yields superior composite properties including resistance to water and bonding of the PVC to the glass such that it is not removed by THF. With respect to other polymers the multisilane can also provide superior bonding by a reaction generating a covalent bond, though the mechanism will be different from the one with PVC.

It should be noted that a VC resin is typically stabilized with a metallo-organic salt or soap, or an organometallic compound having a carbon-to-metal bond, specifically to counter the thermal dehydrohalogenation of the VC resin during thermoforming, and such a stabilizer is essential in my composition. Surprisingly, however, it does not negate the same reaction catalyzed by the multisilane coupling agent.

Desirable film formers are derived from a polymer having (i) an alkyleneimine repeating unit, such as polyethyleneimine; (ii) an amide repeating unit, such as poly(vinyl pyrrolidone); (iii) a triazine-containing repeating unit such as melamine, or a ureyelene (—HNCONH—) repeating unit; (iv) a urethane repeating unit such as in the polymers disclosed in "Aqueous Dispersions of Crosslinked Polyurethanes", by Tirpak, R. E. and Markusch, P. H., *Jour Coating Tech*, pp 49–54, Vol. 58, No. 738, (July '86); (v) an unsaturated polyether unit such as poly(1,methylenefuran); (vi) a cyclic acetal repeating unit such as poly(vinyl butyral); an aminimide repeating unit such as poly(methacrylimide trimethylamine); and, (vii) water dispersible or emulsifiable epoxides such as glycidyl ether bisphenol-A epoxy/diethanolamine.

Most preferred are film formers which are soluble in an aqueous sizing solution, but the method of coating the glass is not critical provided a sufficient amount of film former is deposited to catalyze a reaction in which allylic Cl moieties in the VC resin chain are covalently bonded to an aminosilane. Less preferred are non-aqueous solutions, because of difficulty dealing with an organic solvent economically, and aqueous dispersions which are binary colloid systems in which particles of polymer are dispersed in a continuous phase (water). More preferred because of better stability are emulsions which are colloidal mixtures of two immiscible fluids, one being dispersed in the other in the form of fine droplets, the one preferably being water.

Glass fibers for use herein are conventionally sized with the multisilane and conventional film formers, surfactants, lubricants and the like, but the fibers have unexpectedly shown an improvement in strength of a composite reinforced with them, such that a PVC composite containing 30 wt % glass has a minimum tensile strength of 12,000 psi and an unnotched Izod impact of at least 6.0 ft.lb/$in_2$. Such strength was never before deliberately or reproducibly attained, except in the aforesaid '360 Rahrig patent.

Though the type of glass, and the diameter of the fibers is not critical, relatively soda-free lime-aluminum borosilicate glass, such as "E" and "S" glass is preferred, drawn into filaments having a diameter less than 20 microns, preferably from 10 to about 16 microns.

The length of the filaments, and whether they are bundled into fibers and the fibers bundled, in turn, into yarns, ropes or rovings, or woven into mats, and the like, are not critical to the invention, but it is most convenient to use filamentous glass in the form of chopped strands from about 1 mm to about 27 mm long, preferably less than 5 mm long. In the composition most preferably used for producing pellets in the size range from about 3 mm to about 8 mm in equivalent diameter, which pellets are used to mold shaped articles, even shorter glass fiber lengths, generally less than 1 mm will be encountered because, during compounding, considerable fragmentation will occur, some fibers being as short as 100 microns.

The best properties of the the thermoformed composites are obtained when the glass fibers are present in an amount in the range from about 5% to about 50% by wt, based on the wt of combined glass fibers and resin; and the fibers are in the range from about 500 microns to about 1 mm long. It will be appreciated that less than 5% by wt fibers has little reinforcing value, and more than about an equal part by wt of glass fibers, relative to the amount of VC resin, results in a mixture which cannot be satisfactorily processed.

The multisilane is generally liquid, applied from the reaction mass in which it is formed without separation, and, because the amount to be deposited on the fibers is relatively small, partially hydrolyzed aminosilane is applied to the fibers from a solution, dispersion or emulsion, usually in water, of preselected concentration.

The GFR VC thermoplastic resin composition in the best mode of this invention consists essentially of 100 parts by wt of VC resin, and from 10% to about 35% by wt of glass fibers coated with from 0.2% to about 0.6% by wt of a specified multisilane, and from 0.2% to about 0.6% by wt of a specified film former. If the amounts of each of the foregoing is substantially outside the specified ranges, the moldability and processability of the glass fibers and resin is reduced, and both the dry strength and wet strength are vitiated.

As used herein the term "consists essentially of" means that the named ingredients are essential, though other ingredients which do not vitiate the advantages of the invention can also be included. Such ingredients may include conventional additives such as fillers like talc, mica, clay and the like, light stabilizers, heat stabilizers, antioxidants, pigments and dyes as may be required for a particular purpose, it being recognized that the amount of the additive(s) used will affect the physical properties of the thermoformed composite. The term particularly also includes a lubricant, preferably a cationic lubricant commercially available as an acidified fatty acid amide under the trade designation Emery 6760-U. Such a lubricant is typically present in an aqueous size in an amount in the range from about 0.01% to about 4% by wt of the aqueous composition. It will be appreciated that sizing glass fibers commercially dictates the use of an aqueous size, and it is most unusual to find that the multisilane of this invention is soluble in aqueous size.

Evaluation of the adhesion of glass fiber to VC resin in a composite was done by measuring the composite tensile strengths and the Izod impact strengths, both notched and unnotched. In addition, the scanning electron microscopy was used to examine the fracture surfaces of composite specimens to determine when failure was not cohesive failure.

Though XPS studies of silanes on glass surfaces have been published, none has been published correlating quantitative spectroscopic measurements of fiber-matrix adhesion with microscopic and macroscopic measurments of interfacial strength in GFR composites, particularly short fiber GFR composites.

Such XPS measurements were made with PVC composites in which the PVC was removed by dissolving in THF, then extracted in THF for a week (7 days) using a Soxhlet apparatus. The data presented in Table I herebelow were collected on glass fibers taken from a series of composites in which the film former, and the amount of it used, was not varied, but used at the same weight percent level. The ratio of total Cl, which could only have been derived from the PVC coupled to the glass, to total C was measured as the ratio of Cl(2p)/C(1s) peaks, and these ratios correlated to the tensile strength of each sample, all of which samples contained 30 wt % glass fibers.

The nitrogen percent measured is derived from the multisilane adhered to the glass fiber surface after extraction with THF. The higher the N % the more the multisilane remaining on the surface.

The percent PVC measured is the amount left on the glass fiber surface after extraction with THF, because it is reacted with the multisilane. The more the PVC, the more the bonding to the multisilane.

Preparation of VC Homopolymer Composites for Testing:

All the compounding ingredients except the chopped glass strands were 'powder-mixed' on a Henschel high speed mixer at 3000 rpm for 30 sec. Each powder mixture was then milled on a Getty Model 60 4"×9" electric mill at a mill roll temperature of 215° C. using a roll separation of 0.025". Then 105 g of the powder is fed to the mill and fused in about 1 min after which 44 g of chopped glass fibers about 6.4 mm long, which have been treated with a multisilane and film former were added to the VC homopolymer while milling is continued. The GFR sheets were taken off the mill and labeled to distinguish the mill direction from the transverse direction.

The milled sheets were constant volume molded into 6"×6"×0.05" plaques. In this procedure the mold was preheated to 199° C. for 10 min. Then 65 g of the GFR VC sheet were added to the mold. Care was taken to assure that all mill stock added to the mold was maintained at the same orientation. The mold was then placed into the press and over a 1 min time span, a pressure and release schedule of 5, 10, 20 and 30,000 lbf (pounds force) was followed. The pressure was then pumped to 330,000 lbf a second time and maintained for 1.5 min. The mold was then transferred to a cold press and allowed to cool for 5 min under pressure. Tensile dumbbells were cut and routed from these plaques. Again care was taken to identify sample orientation relative to the mill direction during the operation of these tensile bars.

The following samples identified by numbers in the six hundred series were prepared with the multisilanes specified and Tween 80 as film former. All samples met the criterion of at least 6 ft.lb/in² unnotched Izod, and 12,000 psi tensile (dry), for 30 wt % glass fibers. The samples were compared for notched an unnotched Izod values, the Cl/C ratio, N %, and % PVC remaining on the glass after extraction with THF.

| Sample | Represented by Structure |
|---|---|
| 609 and 611 | 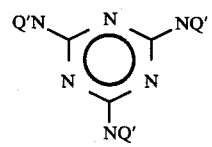 | wherein Q' represents —NH(CH$_2$)$_2$NH(CH$_2$)$_3$Si(OCH$_3$)$_3$ 631 and 634

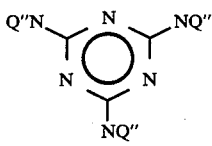

wherein Q" represents —CH$_2$NH(CH$_2$)$_2$NH(CH$_2$)$_3$Si(OCH$_3$)$_3$

The following examples serve to illustrate the principal concepts for preparation of the multisilanes in either an organic or an aqueous medium, which were used in the samples identified hereinabove. It will be appreciated that the reaction of alkoxysilane and triazine-ring containing compound may proceed without providing a mutual solvent for the reactants, but for practical reasons, a mutul solvent for the reactants and the strong acid catalyst, is preferred.

EXAMPLE 1

Preparation of a water-soluble compound (used in the preparation of sample 634) by reaction of hexamethoxymethylmelamine (HEMA) with (CH$_3$O)$_3$Si(CH$_2$)$_3$NH(CH$_2$)$_2$NH$_2$ (A-700 or Z-6020):

Dissolve 10 g of HEMA (0.26 mol) in 100 ml distilled water and add 0.1 g p-toluene sulfonic acid catalyst. To the mixture slowly add 34.16 g A-700 (0.154 mol) in 50 ml water with stirring under argon. Heat to reflux overnight under argon and cool to room temperature.

The resulting triazine-containing multisilane has the structure:

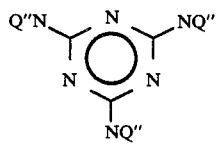

wherein Q" has the same connotation as hereinabove.

Without making any separation, a portion of the reaction mass is mixed with a polymer film former to provide a sizing composition which is coated on glass fibers. The glass fibers are used to reinforce rigid poly(vinyl chloride) PVC. IR and NMR spectroscopic analysis confirms the structure of the multisilane formed, and that all the reactants, provided in stoichiometric ratio, are consumed. The test results are presented in Table I.

EXAMPLE 2

Preparation of a tetrahydrofuran (THF)-soluble triazinecontaining multisilane compound (used in preparation of sample 631) by reaction of HEMA with A-700 or Z-6020:

The same multisilane prepared in Ex 1 hereinabove, except prepared in anhydrous THF, is prepared in a manner analogous to that described hereinabove in Ex 1. The same ingredients in identical amounts were stirred into 150 ml THF, and refluxed under argon at ambient pressure overnight. IR and NMR analysis indicates that all reactants are consumed and the reaction is complete. The product multisilane is present as 15% total solids in the reaction mass. A portion of the reaction mass is removed and the THF removed in a Rotovap. The solid is then analyzed and is found to have the same structure as the multisilane formed in Ex 1 hereinabove.

EXAMPLE 3

Preparation of a tetrahydrofuran (THF)-soluble triazine-containing multisilane compound (used in the preparation of sample 609) by reaction of cyanuric chloride with A-700 or Z-6020:

To a solution of 10.0 g of cyanuric chloride (0.0543 mol) in 100 ml of THF stirred with a magnetic stirrer under argon in a 50 ml round-bottom flask, is slowly added a solution of 116.45 g triethylamine (0.1629 mol) and 39.80 g of A-700 (0.1629 mol) in 50 ml THF. A white precipitate forms which is removed by filtration. The filtrate is used to provide the desired amount of solid multisilane in a size for glass fibers.

It will be appreciated that the preparation in THF is primarily employed to provide the multisilane in a solvent for use in an adhesive composition, not as a size composition for glass fibers, for reasons given hereinabove. The preparation in THF also avoids the formation of polymerization of the multisilane, such as takes place in the presence of water, so that the multisilane may more easily be analyzed, and its structure characterized.

EXAMPLE 4

Preparation of a water-soluble triazine-containing multisilane compound (used in the preparation of sample 611) by reaction of cyanuric chloride with A-700 or Z-6020:

10.0 g of cyanuric chloride (0.0543 mol) powder are suspended in 100 ml of water while stirring with a magnetic stirrer under argon in a 50 ml round-bottom flask to which is slowly added a solution of 116.45 g triethylamine (0.1629 mol) and 39.80 g of A-700 (0.1629 mol) in 50 ml water. The cyanuric chloride gradually reacts, the product dissolving in water as it forms. A white hydrochloride precipitate forms which is removed by filtration. The filtrate is used to provide the desired amount of solid multisilane in a size for glass fibers.

For making a comparison, all composites were prepared in exactly the same manner using 100 parts b wt Geon 110x346 PVC, 30 parts by wt glass fibers, and 3 parts by wt Thermolite 31 dibutyl-tin-bisisooctylthioglycolate stabilizer, but no lubricant was added.

Pellets of the composition of this invention are preferably formed in a pelletizing extruder after the composition is masticated in a Buss Kneader into which the VC resin and other compounding ingredients are fed, as described in the '360 patent. The pellets may then be extruded or pultruded. Sheets of GFR PVC may be prepared by impregnating glass mat, sized as described hereinabove, with PVC so that there is about an equal weight of resin and glass fibers in each sheet. Several such sheets cut to a predetermined configuration are stacked in a mold and conventionally molded at a temperature of 160°–200° C. and a pressure of about 1000 psi (about 30,000 lbf) to form a shaped article.

The comparative data for samples 609, 611, 631 and 634 are set forth in the following Table. The control is a sample prepared with E glass fibers coated with A-700 and a poly(ethylene oxide:propylene glycol) film former as described in the Rahrig '360 patent. All samples have tensile strengths (dry) at least as great as the control (13,000 psi). The Izod values in all cases are the average of five samples and the deviation is ±0.2 for notched, and ±1.0 for unnotched.

TABLE

| Sample No. | Izod* notched | Izod* unnotched | XPS Cl(2p)/C(1s) | N% | PVC% |
| --- | --- | --- | --- | --- | --- |
| Control | 2.09 | 6.75 | 0.946 | 0.00 | 72.0 |
| 634 | 1.83 | 8.79 | 1.05 | 0.47 | 84.0 |
| 631 | 2.04 | 8.07 | 1.07 | 0.34 | 86.0 |
| 609 | 1.69 | 9.06 | 0.88 | 1.4 | 68.0 |
| 611 | 1.95 | 9.55 | 0.83 | 1.7 | 74.7 |

*Izod measured in ft.lb/in$^2$

In an analogous manner, composites are made from CPVC and cut into tensile bars. An improvement in tensile strength of a GFR CPVC sample is obtained not only with a variety of polyoxyalkylene polyols which are popular for commercial production, but also with other polymer film formers so long as the polymer film former used satisfies the basicity and Cl/C ratio set forth hereinabove.

EXAMPLE 5

Preparation of a polyurethane adhesive for a glass surface:

A multisilane was prepared as described in Example 2 hereinabove and the reaction mass allowed to stand for about an hour. The aged reaction mass is used to prepare a polyurethane adhesive for adhering a laminar glass surface to any other laminar surface, preferably of a synthetic resinous rigid material, or, of an elastomeric material such as a silicone rubber, or natural or synthetic styrene-butadiene rubber (SBR).

100 parts by weight of A1503 polyurethane and 5 parts by wt of A1343 polymethylene polyphenyleneisocyanate (PAPI), both commercially available from The B. F. Goodrich Company, are dissolved in a solvent for the polyurethane such as tetrahydrofuran or N-methyl-pyrrolidone, to produce a 50%-70% solids solution. To the solution is added from about 5% to about 10% by weight of a multisilane, based on the weight of the solution, and thoroughly mixed. The multisilane-containing solution of the polyurethane is then coated onto a glass surface over an area corresponding to the area of the other material to which the coated glass is to be adhered. Pressure is applied to force the glass surface against that of the other material and the solvent is evaporated while the surfaces are under pressure.

The adhesive solution is brushed onto one surface of a sheet of glass 10.16 cm, that is 4" (ins) square, and 63.5 mm (0.25"), thick, and clamped against a piece of polyurethane 10.16 cm square and 63.5 mm thick. The clamped assembly is placed in an oven at 200° C. for 15 min and removed. Upon cooling, an attempt to shear the glass away from the polyurethane results in a portion of the polyurethane being torn away from the square polyurethane sheet, indicating the bond between the glass and the polyurethane is stronger than that of polyurethane to polyurethane. Such bonding has particular application in the fabrication of automobile windows, and other applications in which a glass surface is to be bonded to polyurethane.

In an analogous manner, another square sheet of glass of the same dimensions, on which sheet the adhesive is brushed, is clamped to a piece of rigid PVC of the same dimensions and placed in the oven at the same temperature for the same time. Upon cooling, an attempt to shear the glass away from the PVC results in a thin sheet of glass being torn away from the thick glass square sheet, the thin sheet adhering to the PVC, which indicates cohesive bonding between the glass and PVC surfaces.

In an analogous manner it is found that excellent bonding is obtained with the adhesive and 10.16 cm square blocks of the various following materials in arbitrary thicknesses ranging from about 0.25 in thick to about 2.54 cm (1 in): (a) a polycarbonate sheet commercially available as Lexan; (b) a polymethylmethacrylate sheet commercially available as Lucite; (c) a block of vulcanized natural rubber; (d) a block of unpainted smoothly finished wood; (e) a block of aluminum metal; and (f) a block of steel.

EXAMPLE 6

Preparation of an epoxy resin adhesive for a glass surface:

A multisilane was prepared as described in Example 2 hereinabove and the reaction mass allowed to stand for about an hour. The aged reaction mass is used to prepare a epoxy resin adhesive for adhering a laminar glass surface to any other laminar surface, preferably of a synthetic resinous rigid material, or, of an elastomeric material such as a silicone rubber, or natural or SBR.

100 parts by wt of Epon 828 epoxy, commercially available from The Shell Chemical Company, is mixed with 40 parts of Versamid 115 amide curing agent (from General Mills), and the resin formed is dissolved in a solvent for the epoxy such as methylethylketone (MEK), to produce a 0%-70% solids solution. To this solution is added from about 5% to about 10% by weight of a multisilane, based on the weight of the solution, with thorough mixing.

The multisilane-containing solution of the epoxy is then coated onto a continuous bundle of glass fibers, sized for use with an epoxy resin, by passing the fibers through a bath of the solution before the fibers are wound onto a mandrel in the shape of a drum, in a conventional filament-winding operation.

EXAMPLE 7

Preparation of a vinyl acetate adhesive for a glass surface:

A multisilane was prepared as described in Example 2 hereinabove and the reaction mass allowed to stand for about an hour. The aged reaction mass is used to prepare a vinyl acetate adhesive for adhering a laminar glass surface to any other laminar surface, preferably of a synthetic resinous rigid material, or of an elastomeric material such as a silicone rubber, or natural or SBR.

Vinyl acetate is dissolved in a solvent such as THF, to produce a 50%-70% solids solution. To this solution is added from about 5% to about 10% by weight of a multisilane, based on the weight of the solution, with thorough mixing. The multisilane-containing solution of the vinyl acetate is then coated onto a glass surface over an area corresponding to the area of the other material, specifically SBR, as described hereinabove. Pressure is applied to force the glass surface against that of the SBR, and the solvent is evaporated while the surfaces are under pressure, to obtain an excellent bond between the glass and SBR.

EXAMPLE 8

Preparation of a protective coating for a solid surface:

A multisilane was prepared as described in Example 2 hereinabove and the reaction mass allowed to stand for about an hour. The aged reaction mass is used to prepare a protective coating for polished aluminum by brushing a 2%–5% by wt solution of the multisilane in THF onto the aluminum surfaces to be protected. Upon evaporation of the solvent, the aluminum surface is protected against usual attack upon weathering. In an analogous manner, the cutting edges of drill bits, and the surfaces of various machine tools made of tool steel may also be protected.

It should be noted that in the foregoing examples, either cyanuric chloride or HEMA are the triazine ringcontaining compounds because they are commercially available. As illustrated, an organic amine base, such as triethylamine or pyridine, is used to neutralize the HCl formed when cyanuric chloride is used; and a Bronsted acid such as camphor sulfonic acid is used when the triazine ring carries alkoxyalkylamine groups. Other triazine ringcontaining compounds with substitutable 2, 4 and 6 positions may be used with an appropriate choice of catalyst to effect the desired substitution with the alkoxysilane of choice.

I claim:

1. A triazine-ring containing multisilane having a structure selected from

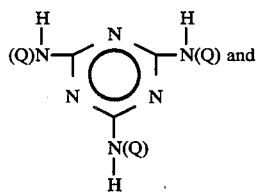 and

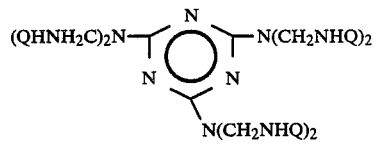

wherein Q represents

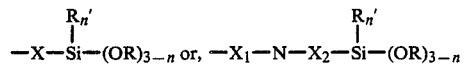

wherein X, $X_1$, and $X_2$ represents a divalent radical selected from the group consisting of $C_1$–$C_{10}$ alkylene $$-(CH_2)_{1-10},$$

and $C_6$–$C_{20}$ aralkyl;

R represents $C_1$–$C_5$ lower alkyl;

R′ represents H, $C_1$–$C_8$ alkyl, phenyl, or $C_7$–$C_{18}$ aralkyl; and, n has a value of 0 or 1.

2. The multisilane of claim 1 wherein said Q is the radical of an alkoxysilane selected from the group consisting of 3-aninopropyl-triethoxysilane, $H_2N-(CH_2)_3-Si-(OC_2H_5)_3$;

aminomethyl-triethoxysilane, $H_2N-(CH_2)-Si-(OC_2H_5)_3$;

2-aminoethyl-aminopropyl-trimethyoxysilane, $H_2N-(CH_2)_2-NH-(CH_2)_3-Si-(OCH_3)_3$; and, 2-aminoethyl-aminopropyl-methyl-dimethoxysilane,

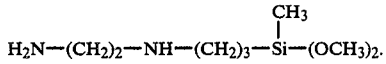

* * * * *